United States Patent [19]

Drake et al.

[11] Patent Number: 4,473,545

[45] Date of Patent: Sep. 25, 1984

[54] COMPOSITE MATERIALS

[75] Inventors: Cyril F. Drake, Harlow; Ronald Jones, Sawbridgeworth, both of England

[73] Assignee: Standard Telephones and Cables PLC, New York, N.Y.

[21] Appl. No.: 442,723

[22] Filed: Nov. 18, 1982

[30] Foreign Application Priority Data

Nov. 18, 1981 [GB] United Kingdom ............... 8134751

[51] Int. Cl.³ ..................... A61K 9/26; A61K 9/22; A61K 9/32

[52] U.S. Cl. ........................... 424/22; 424/19; 424/32

[58] Field of Search .................. 424/19, 22, 32, 78

[56] References Cited

U.S. PATENT DOCUMENTS

| | | | |
|---|---|---|---|
| 3,880,990 | 4/1975 | Bauer et al. | 424/19 |
| 4,001,389 | 1/1977 | Fildes | 424/19 |
| 4,177,255 | 12/1979 | Dannelly | 424/32 |
| 4,181,708 | 1/1980 | Dannelly | 424/32 |
| 4,181,709 | 1/1980 | Dannelly | 424/32 |
| 4,181,710 | 1/1980 | Dannelly et al. | 424/32 |
| 4,196,187 | 4/1980 | Dannelly et al. | 424/33 |
| 4,199,561 | 4/1980 | Roth et al. | 424/81 |
| 4,234,565 | 11/1980 | Flodin et al. | 424/33 |
| 4,256,785 | 5/1981 | Dannelly | 426/89 |
| 4,322,398 | 3/1982 | Reiner et al. | 424/19 |

*Primary Examiner*—Frederick E. Waddell
*Attorney, Agent, or Firm*—James B. Raden

[57] ABSTRACT

An animal feed additive comprises a composite of a relatively insoluble binder, a particulate soluble material and an active material. The particulate material is such that it is readily soluble under a particular range of pH conditions, e.g. under said conditions. Dissolution of the particulate material renders the binder water permeable thus permitting release of the active material.

8 Claims, No Drawings

COMPOSITE MATERIALS

This invention relates to devices for supplying an active material at a controlled rate into an aqueous medium.

Domesticated animals, for example pigs and poultry, are often supplied with feed additives to encourage growth and/or to maintain the animal in a healthy condition. A particularly important feed additive is the amino acid methionine (α-amino-γ-methylthio-n butyric acid) which is essential to healthy growth. This material cannot however, with present techniques, be utilised effectively by ruminant animals. Food eaten by a ruminant remains in the rumen, where it is exposed to natural bacterial action, for periods up to 24 hours after which it is passed through the remainder of the digestive system in about 1 hour. It has been found that if methionine is fed to a ruminant the material is substantially completely consumed by the rumen bacteria before it can be absorbed by the animal. It is not possible with present techniques to delay release of methionine from a feed additive until the material has reached the post-rumen part of the digestive system.

The object of the present invention is to minimise or to overcome this disadvantage.

According to one aspect of the invention there is provided a device for oral administration to a ruminant animal and comprising an active material contained or incorporated in a carrier body, wherein said carrier body is relatively insoluble under the low acidity rumen conditions and is relatively soluble under the high acidity post-rumen conditions.

We have found that certain active materials, for example methionine may be supplied e.g. to a ruminant animal in the form of a pellet or granules wherein the active material is contained in a composite material comprising a substantially insoluble food grade polymer and a water soluble particulate material. The composition of the particulate material is chosen such that it is substantially insoluble in the near neutral (pH 6) conditions in the rumen but is highly soluble in the appreciably acid conditions (pH 2) pertaining in the post-rumen part of the alimentary canal.

When the structure is immersed in an aqueous medium the particulate material dissolves to provide a series of passageways through the polymeric material thus permitting the ingress of water. Such a structure can be employed for the delayed and controlled dissolution of an active material that, prior to the dissolution of the particulate material and the consequent significant increase in the water penetrability of the polymer, is protected by the polymer from dissolution.

Advantageously the soluble particulate material is a soluble glass composition or a mixture of such glass composition. Water soluble glass compositions have the important property that their dissolution rate may be tailored to a desired value by minor composition adjustment thus providing for the manufacture of composite structures with a wide range of dissolution properties.

We prefer to employ phosphate glasses for this purpose as such materials are relatively non-toxic and also relatively simple to prepare. Furthermore, the techniques for controlling the dissolution rate of these glass systems are well understood. The glasses generally comprise phosphorus pentoxide, as the glass forming oxide of the glass together with one or more further oxides which provide the glass modifying constituents of the composition. The dissolution rate, and the pH of solutions of such compositions are determined by the nature and proportion of the glass modifying oxide or oxides and by the overall molar ratio of glass modifier to glass former.

We have also found that the presence of certain metal oxides, for example oxides of most two or three valent metals, reduces the dissolution rate of a glass composition whilst the presence of other metal oxides, in particular alkali metal oxides, increases the dissolution rate. Thus, by suitable adjustment of the ratio of glass-formers to glass modifiers and the proportions of these two types of oxides any desired dissolution rate can be obtained. The techniques of glass dissolution rate and solution pH control are more fully described in U.S. Pat. No. 4,350,675. Moreover, the relative solution rate of the glass at different pHs is determined by the glass composition. Typical of suitable glass compositions, but by no means limiting are glasses of the general type $xM_2O:yMO_{(100-x-y)}P_2O_5$ where $M_2O$ comprises one or more alkali-metal oxides, MO comprises one or more oxides selected from MgO, CaO, ZnO, and FeO. Minor amounts of other glass-formers such as $Al_2O_3$ and $SiO_2$ may be present. X and y are molar proportions.

Two typical glass compositions are:
$Na_2O$: 40.6 mole %
$K_2O$: 1.2 mole %
CaO: 8.4 mole %
ZnO: 7.9 mole %
$P_2O_5$: 41.9 mole % which has dissolution rates at pH2 and pH6 in the ratio 3:1 and:
$Na_2O$: 45.2 mole %
$K_2O$: 1.4 mole %
CaO: 10.1 mole %
MgO: 2.0 mole %
$P_2O_5$: 41.3 mole % which has dissolution rates at pH2 and pH6 in the ratio 12:1.

The polymer may comprise a wide variety of materials. We prefer to employ cellulosic materials, but other materials may of course also be employed. Typical of such polymers, though by no means limiting, are polyenes, polyesters, polyamides, polysaccharides, natural gums and latexes, polyamides, polysaccharides, and mixtures and copolymers thereof. The polymer matrix may be thermosetting or thermoplastic. Furthermore, in some applications, the polymer may be cross-linked in any of the known techniques.

The active material may be dispersed in the polymer-powdered glass composite, or a body comprising or containing the active material may be encapsulated in the polymer/glass composite. When the device is administered to a ruminant animal it remains in the rumen for a period of up to 24 hours during which time substantially no dissolution of the glass takes place. The device is then passes to the post-rumen wherein the relatively acid conditions pertaining therein cause rapid dissolution of the glass permitting consequent release of the active material.

In a particularly advantageous arrangement the active material is granular and is formed into a body wherein the granules are cemented together by a composite comprising a polymer and a powdered water soluble glass. The glass particles are significantly smaller than the active material granules so that the composite acits as a 'mortar' between the granules thus providing a coherent body. The body may be formed e.g. by pressing, extraction or casting and may be subsequently comminuted.

When such a body is immersed in an aqueous medium of suitable pH the glass particles dissolve at a controlled rate to provide an array of interconnecting voids in the polymer. The active material can then dissolve through these voids.

Typically a pellet or granular material for oral consumption by a ruminant animal may be made by mixing a solid or liquid polymer with a finely divided glass composition and a granulated active material. Where the active material is a liquid at ambient temperatures it may be absorbed on a solid carrier such as activated silica or bentonite clay. After thorough mixing has been effected the composition is formed into solid coherent bodies by pressing, extrusion or casting. In such a pellet or granular material the major volume proportion may comprise active material.

We claim:

1. In a feed composition adapted for oral administration to a ruminant animal, the composition including a biologically active material to be introduced into the post-rumen portion of the digestive system of said animal, said biologically active material being incorporated in a composite carrier body consisting essentially of a polymeric material and a particulate glass composition, said polymeric material being essentially insoluble in both the rumen and the post-rumen portion of the digestive system of said animal, said active material being shielded from release out of said carrier body into said rumen and being releasable at a controlled rate into said post-rumen through passageways formed in said carrier body by the dissolution at a controlled rate of said particulate glass composition when said feed composition enters said post-rumen portion of said digestive system;

the improvement in which said particulate glass composition comprises a phosphate glass corresponding to the formula;

$$xM_2O{:}yMO_{(100-x-y)}P_2O_5$$

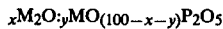

wherein x and y are molar proportions; $M_2O$ is an alkali metal oxide or mixture of alkali metal oxides and MO is an oxide selected from the group consisting of MgO, CaO, ZnO, FeO and mixtures thereof, said phosphate glass being essentially insoluble in said rumen but being soluble at a controlled dissolution rate in said post-rumen whereby said passageways are formed in said carrier body.

2. In a feed additive for a ruminant animal said additive including a composite of a granular biologically active material, a powdered glass material and a polymer;

the improvement in which said powdered glass material comprises a phosphate glass corresponding to the formula:

$$xM_2O{:}yMO_{(100-x-y)}P_2O_5$$

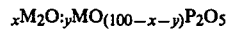

wherein x and y are molar proportions; $M_2O$ is an alkali metal oxide or mixture of alkali metal oxides and MO is an oxide selected from the group consisting of MgO, CaO, ZnO, FeO and mixtures thereof, said phosphate glass being substantially insoluble under the pH conditions pertaining in the rumen but being soluble under the pH conditions pertaining in the post rumen whereby dissolution of said glass material increases the water penetrability through said composite thereby providing a dissolution path for the active material.

3. A feed additive as claimed in claim 2 wherein the active material is methionine.

4. A feed additive as claimed in claim 2, wherein the active material is a liquid absorbed on to activated silica or a bentonite clay.

5. The composition of claim 1 wherein said biologically active material is methionine.

6. The composition of claim 1 wherein said polymeric material is selected from the group consisting of cellulosic polymers, polyenes, polyesters, polyamides, polysaccharides and mixtures and copolymers thereof.

7. The composition of claim 1 wherein said phosphate glass comprises 40.6 mole percent $Na_2O$; 1.2 mole percent $K_2O$; 8.4 mole percent CaO; a 7.9 mole percent ZnO and 41.9 mole percent $P_2O_5$.

8. The composition of claim 1 wherein said phosphate glass comprises 45.2 mole percent of $Na_2O$; 1.4 mole percent $K_2O$; 10.1 mole percent CaO; 2.0 mole percent MgO and 41.3 mole percent $P_2O_5$.

* * * * *